US008684970B1

(12) United States Patent
Koyfman et al.

(10) Patent No.: US 8,684,970 B1
(45) Date of Patent: Apr. 1, 2014

(54) STEREOTACTIC SHOCKWAVE SURGERY AND DRUG DELIVERY APPARATUS

(75) Inventors: Yakov U. Koyfman, Wilmington, DE (US); Gabriel Eidelman, Rockville, MD (US)

(73) Assignee: Medical Shockwaves Inc., Wilmington, DE (US)

( * ) Notice: Subject to any disclaimer, the term of this patent is extended or adjusted under 35 U.S.C. 154(b) by 5 days.

(21) Appl. No.: 13/404,973

(22) Filed: Feb. 24, 2012

Related U.S. Application Data

(60) Provisional application No. 61/518,055, filed on Apr. 30, 2011.

(51) Int. Cl.
*A61M 37/00* (2006.01)

(52) U.S. Cl.
USPC ........................................ 604/140; 604/145

(58) Field of Classification Search
USPC ........ 604/23–25, 131, 140, 145–147; 60/208, 60/212, 214, 217, 248
See application file for complete search history.

(56) References Cited

U.S. PATENT DOCUMENTS

| | | | | |
|---|---|---|---|---|
| 2,958,716 | A * | 11/1960 | Lahr et al. | 204/157.62 |
| 4,813,402 | A * | 3/1989 | Reichenberger et al. | 601/4 |
| 4,823,773 | A * | 4/1989 | Naser et al. | 601/4 |
| 5,700,245 | A * | 12/1997 | Sancoff et al. | 604/145 |
| 5,947,928 | A * | 9/1999 | Muller | 604/140 |
| 6,494,034 | B2 * | 12/2002 | Kaemming et al. | 60/248 |
| 6,755,821 | B1 * | 6/2004 | Fry | 606/15 |
| 7,351,220 | B2 * | 4/2008 | Chiwanga et al. | 604/69 |
| 7,559,917 | B2 * | 7/2009 | Alexandre et al. | 604/143 |
| 7,798,989 | B2 * | 9/2010 | Alexandre et al. | 604/68 |
| 8,070,714 | B2 * | 12/2011 | Alexandre et al. | 604/69 |
| 2006/0036195 | A1 * | 2/2006 | Schultheiss et al. | 601/2 |
| 2007/0239082 | A1 * | 10/2007 | Schultheiss et al. | 601/4 |
| 2011/0126511 | A1 * | 6/2011 | Glaser et al. | 60/248 |

OTHER PUBLICATIONS

Abstracts, ISMST 10th International ISMST Congress Toronto 2007.
Abstracts, ISMST 11th International ISMST Congress Juan les Pins 2008.
S. Bao, B. D. Thrall, R. A. Gies, and D. L. Miller, In Vivo Transfection of Melanoma Cells by Lithotripter Shock Waves, Cancer Research 58, 219-221, Jan. 15, 1998.
T. Kodama, A. G. Doukas, M. R. Hamblin, Delivery of ribosome-inactivating protein toxin into cancer cells with shock waves, Cancer Letters 189, 69-75, 2003.
A. Warlters, D. L. Morris, A. Cameron-Strange, W. Lynch , Effect of electrohydraulic and extracorporeal shock waves on gastrointestinal cancer cells and their response to cytotoxic agents., Gut, 1992, 33, 791-793.

* cited by examiner

*Primary Examiner* — Quynh-Nhu H Vu

(57) ABSTRACT

A therapeutic apparatus for treating body tissue comprises a vessel enclosing a detonation chamber into which a detonatable mixture is introduced and then detonated using an igniter to form at least one shockwave and/or acoustic wave. A wave guide assembly having a converging geometry directs the wave to a tip of the wave guide assembly that is placed in contact with tissue to be treated by the wave. The wave guide assembly may include a wave focusing section surrounding the vessel, a flexible conduit connected to the wave focusing section and a needle connected to the conduit and sized for insertion into patient tissue to be treated. A cap connected to the end of the needle is formed from material permitting the wave or waves generated in the detonation chamber to pass therethrough to treat the patient tissue into which the needle is inserted.

20 Claims, 6 Drawing Sheets

STEREOTACTIC SHOCKWAVE SURGERY AND DRUG DELIVERY APPARATUS

PRIORITY CLAIM

The present application claims the benefit of priority of U.S. provisional application No. 61/518,055 filed Apr. 30, 2011, which is incorporated herein by reference

BACKGROUND OF THE INVENTION

1. Field of the Invention

The present invention generally relates to an apparatus and to a method for treating biological substances by shockwaves or high amplitude acoustic waves. More particularly, the present invention is in the technical field of an apparatus and to a method that use shockwaves for surgery and drug delivery.

2. Description of Related Art

Use of shockwaves or high pressure amplitude acoustic waves in medical procedures is known. U.S. Pat. No. 4,823,773 to G. Naser et al. discloses generation of focused shockwaves with an extracorporeal lithotripter using an array of piezoelectric emitters that allow shattering of calculi in a patient. Extracorporeal shock waves (ESW) can also be generated electro-hydraulically using electrical discharges in liquids as discussed in Patent Application Pub. No. U.S. 2006/0036168 by Shen-Min Liang et al. ESW are used in numerous medical applications including breaking kidney stones, treatment of plantar fasciitis, chronic tendinitis, chronic prostatitis, and other medical conditions (Abstracts, ISMST 10th International ISMST Congress Toronto 2007). ESW cannot be used for treatment of sensitive areas of the body such as the brain due to difficulty in limiting the shockwave effect to a small area. Shock waves generated by ESW devices will lead to rupture of blood vessels, edema, apoptosis and other tissue damage in the large area around the focal point of the device which is not acceptable for most brain treatments.

U.S. Pat. No. 6,562,004 to A. Doukas et al. discloses a device for transdermal drug delivery that uses detonations of solid explosive energetic materials to generate shockwaves that are transmitted into a drug delivery chamber that is in contact with the skin. The device utilizes a single detonation of a layer of solid explosives that are permanently imbedded into the detonation chamber, thus the device is a single action disposable device.

In Patent Application Publication No. U.S. 2007/0239082, R. Schultheiss et al. disclose a system for treating an internal organ that has a generator source for producing a shock wave connected to a handheld or small shock wave applicator device. The shockwaves are generated by an electrical discharge in liquid contained in the shock wave applicator device and transmitted to the internal organs through a membrane where some areas of the devices are shielded with shock wave absorbing materials or an air gap. External shockwave generation devices based on electrical discharge are not desirable because of damage that can be inflicted to large areas at high pressure levels. In U.S. Patent Application Publication No. U.S. 2006/0036195 R. Schultheiss et al. disclose devices for shock therapy for organs where the entire piezo-ceramic pressure/shockwave generation devices are directly inserted near or into internal organs which is undesirable because it presents a number of limitations on device size and, shockwave intensity and other parameters.

In U.S. Patent Application Publication No. U.S. 2009/0221940, E. H. Marlinghoust et al. disclose an apparatus that generates shock waves by a projectile that collides into an impact body that transmits shock waves into a biological substance. The device produces so called radial shock waves that expand outward from the contact point with the device. The shock waves generated by such a device will have low amplitude and relatively large durations because of inertia of the mechanical projectile.

In U.S. Patent Application Publication No. U.S. 2011/0034832, I. Cioanta et al. disclose a shock wave applicator that includes a shock wave generator and an asymmetrical reflector that enables focusing shock waves at different parts of the body. Although the merits and physics of shock generation or shock reflection are not shown, this patent application describes possible uses of shock waves in medical procedures including: use of shock waves to destroy plaque in blood vessels, treatment of heart muscles, removal of fluid accumulation in the heart, a combination of shockwave treatment with drugs for removing plaque from blood vessels, use of shock waves for dissolution of fat cells, use of shockwaves to create and increase circulation in the colon, and the use of shock waves to promote healing.

U.S. Pat. No. 5,947,928 to D. F. Muller discloses a drug delivery system including a drug delivery initiator for generating a shock wave and a membrane receiving the shock wave and transmitting the shock wave to a material. In operation, rapid opening of a divider causes a shock wave to be generated as pressurized gas is released from the proximal chamber into the distal chamber. The shock wave is then transmitted through the distal opening of the initiator to impinge on the membrane which, in turn, transfers the shock wave to the biological material. Impact of the shock wave on the skin increases the porosity of any of the bio-membranes at or below the skin, thereby enhancing absorption of the drug. In this type of device, the peak pressure as well as shockwave duration will be limited by the pressure difference and rate of opening of the divider between the chambers. The rate of the pressure rise facilitated by the valves will not be sufficient for creation of shockwaves that typically have less than microseconds for the pressure to rise form ambient to peak values. Use of a bursting membrane between the proximal and distal chambers will increase the rate of pressure increase, however it will allow only a single shock wave creation, thus making this device a single use device.

The field of applications of the shock waves in medicine is very broad and includes drug delivery, killing cancer cells, promoting bone healing and others. However, despite the clearly demonstrated effectiveness of using high-intensity shockwaves for medical applications, in practice the use of shockwaves is limited to ether breaking kidney stones where damage to surrounding tissue can be tolerated, or treatment of plantar fasciitis and chronic tendinitis where multiple small energy shockwaves are applied for general stimulation and pain relief. Use of shockwaves for killing cancer cells and bacteria in the internal organs although shown in in vitro studies (S. Bao, B. D. Thrall, R. A. Gies, and D. L. Miller, In Vivo Transfection of Melanoma Cells by Lithotripter Shock Waves, Cancer Research 58, 219-221, Jan. 15, 1998.) is not practical due to lack of capability to generate and deliver high intensity shock waves with high spatial accuracy to the targeted area. Drug delivery using shock waves was demonstrated only for transdermal delivery using laser generated shock waves (T. Kodama, A. G. Doukas, M. R. Hamblin, Delivery of ribosome-inactivating protein toxin into cancer cells with shock waves, Cancer Letters 189, 69-75, 2003.). This technique cannot be applied for drug delivery to internal organs. Use of electromechanical transducers, pressure driven pellets, or electric discharge limit pressure amplitude, shock waves durations and accuracy of shockwave targeting which limits their applications. Use of solid explosive or other high energy density material as disclosed in U.S. Pat. No. 6,562,004 for drug delivery is dangerous and impractical because of regulations governing use and applications of solid explosives. Also use of explosives leads to a single action device which is not practical for many applications.

Thus, there is a critical need for efficient generation of high intensity shockwaves for medical applications. The present invention contemplates elimination of the drawbacks associated with prior art apparatus and methods for generating shockwaves for medical applications.

It is therefore an object of the present invention to provide a method and apparatus for efficient generation of shockwaves with a wide range of amplitudes and positive phase durations and the accurate delivery of such shockwaves to targeted internal or external body area.

It is another object of the present invention to provide a method and apparatus for surgery and drug delivery locally and systemically that will enable direct application of high-intensity shockwaves to cancer tumors or other areas of the body through small-diameter shockwaves guides.

A further object of the present invention is to provide a method and apparatus for surgery that will enable direct delivery of shockwaves wherein the peak pressure and impulse can be adjusted based on application need.

Another object of the present invention is to provide a method and apparatus for surgery and drug delivery locally and systemically that can be image guided to treat different areas of the body.

Another object of the present invention is to provide a method and apparatus that will allow application of shockwaves while preserving or minimizing damage to eloquent areas of the internal organs such as the brain or others where the areas adjacent to a target intended for shockwaves treatment will not be damaged.

Another object of the present invention is to provide a method and apparatus that will be compatible with MRI or similar visualization technology.

SUMMARY OF THE INVENTION

These and other objects of the present invention are achieved by providing a method and apparatus for Stereotactic Shockwave Surgery (SSS) that includes the steps of generating high pressure shockwaves in a shock generation section of the apparatus through the rapid reaction of reactive mixtures, transmitting these waves through a membrane and then through a shockwave guide apparatus and to the biological tissue to be treated either intra-corporeally or extra-corporeally. The apparatus is capable in generating shockwaves or high pressure acoustic waves exiting the shockwave guide with peak pressure values between 0.1 MPa to 1000 MPa and positive phase duration of 10 nanosecond to 100 µsec, that will kill cancer cells, kill all or a substantial number of microorganisms, promote growth of bone, promote tissue healing, assist drug delivery locally and systemically by increasing permeability of cell membranes, remove or substantially weaken brain/blood barriers and cause other known therapeutic effects that are caused by shockwaves or high pressure acoustic waves of various intensity and duration.

Following the shockwave generation stage, the reaction products can be discharged through a pressure relief valve or other pressure relief device into the atmosphere or a products collection tank. After discharge of the detonation products the shockwave generation steps can be repeated as many times as needed for producing medical therapeutic effects or killing cancer cells or microorganisms.

In one embodiment the shockwave surgical apparatus comprises a shockwave generation chamber, valves or other means for controlled injection of fuel and oxidizer, an igniter, a membrane that seals the shockwave generation chamber, a shockwave guide that transports the shockwaves transferred through the membrane to the targeted area of the body. The volume of the shockwave generation chamber may range from 0.1 $cm^3$ to 100 $m^3$, but usually from 1 $cm^3$ to 0.1 $m^3$ and the length of the shockwave guide is preferably 1 cm to 100 m but usually from 10 cm to 5 m. Such a wide range of scales of implementation facilitated by using a detonatable mixture that can be injected into the shockwave generation chamber of an apparatus that is designed to contain detonation products after detonation is critical for various medical applications.

In another embodiment, the shockwave surgical apparatus comprises a shockwave generation section, valves or other means for controlled injection of fuel and oxidizer into the shockwave generation section, an igniter, and a pressure relief valve. A part or all the shockwave generation section is enclosed in liquid or other shockwave transmitting media where the shock waves generated inside the shockwave generation section are transmitted through its wall into the liquid or other shockwaves transmitting media that further delivers shockwaves through one or more shockwave guides to the biological tissue either intra-corporeally or extra-corporeally. To generate high pressure shockwaves at the exits of one or more shockwave guides, the detonatable mixture with an average material density greater than 1 $kg/m^3$ and smaller than 3000 $kg/m^3$ is injected into the shockwave generation section before detonation. After detonation, the shockwave transmitted through the walls of the shockwave generation section will have a peak pressure of 1 MPa to 1000 MPa and a positive phase duration of 50 nanosecond to 100 µsec. These shockwaves will be transmitted through single or multiple shockwave guides into biological tissue and will kill a substantial number of microorganisms, kill cancer cells, cause drugs to be transferred though cell membranes and result in other known therapeutic effects that are caused by shockwaves. Such a wide range of pressures can be achieved by injecting a suitable detonatable mixture into the shockwave generation section of the shockwave surgical apparatus that is designed to contain detonation products during and after detonation and is critical for various medical applications.

In another embodiment, the shockwave surgical apparatus comprises a shockwave generation section and shockwave delivery guides. In this embodiment, a detonatable mixture in the shockwave generation section is produced by electrolysis of a water based electrolyte. Electrical power supplied to the apparatus to decompose water in an electrolysis cell located inside or outside of the shockwave generation section. Water decomposition generates oxygen and hydrogen gases that fill the volume of the shockwave generation section. These gases are mixed and ignited. Ignition of the hydrogen/oxygen mixture generates a shockwave in the shockwave generation section. This shockwave is transmitted through the walls or wall of the shockwave generation section into a liquid media contained in the shockwave guides that deliver the shockwaves to targeted locations either intra-corporeal or extracorporeal. After detonation the detonation products, which will be composed primarily of water vapor, condense into liquid water that can be used in the next shockwave generation cycle. Alternatively, the water vapor generated by the detonation process can be evacuated from the shockwave generation chamber via a gas relief valve and a new quantity of liquid water can be injected into the water electrolysis section of the apparatus for use in the next shockwave generation cycle.

This embodiment of the shockwave surgical apparatus allows operation without using reactive gases, does not emit detonation products and particularly attractive for applications in offices outside of a hospital setting.

In another embodiment, the shockwave surgical apparatus comprises two or more shockwave generation sections that are formed within a chamber filled with liquid or other shockwaves transmitting media. In this embodiment, a detonatable mixture is injected simultaneously or with a time delay into the multiple shockwaves generation sections where reactions are initiated simultaneously or with a time delay. Multiple shockwave generation sections create multiple shock waves or acoustic waves that propagate into shockwave conducting guides that allow transmission to intra-corporeally or extra-corporeally located tissue.

The steps of the shockwave generation and transmission cycle can be applied in a shockwave surgical system once or multiple times depending on a variety of factors including safety requirements, the type of medical therapy to be performed and other factors.

BRIEF DESCRIPTION OF THE DRAWINGS

The present invention will now be described in more detail with reference to preferred embodiments of the invention, given only by way of example, and illustrated in the accompanying drawings in which.

DETAILED DESCRIPTION OF THE INVENTION

In addition to their ordinary meaning, the terms set forth below and as used herein may be defined as follows:

"Shock generation section" or the "first section" is the section of the apparatus where shockwaves are generated including as a result of chemical reaction.

"Shock guide" or the "second section" is the section of the apparatus to which the shockwaves generated in the first shock generation section are transmitted and which facilitate their propagation to the application area;

"Shockwave", "shockwaves", "shock" or "pressure wave" when used in relation to processes in the shock generation section of the apparatus all describe gas dynamic shock waves or waves created by reaction of a detonatable mixture that propagates with supersonic speed.

"Shockwave", "shockwaves", "pressure wave", "shock" or "wave" when used in relation to processes in the shock transmitting section, shockwave guides and other section of the apparatus all describe hydrodynamic shock waves or acoustic waves that propagate with sonic or supersonic speed in liquid or solid media.

"Detonation" or "detonation process" are similar terms and are used herein to describe a physical and chemical phenomena characterized by a rapid chemical reaction that leads to the creation of a shockwave, shockwaves or pressure waves. When used in relation to the process within the first section, i.e., the shock generation section, of the apparatus these terms are used to describe a reactive process that generates a shockwave, shockwaves or pressure waves. It is understood that, as a function of chemical composition, quantities, initial pressure and temperature, different types of chemical reactions including deflagration, detonation, and transition from deflagration to detonation, rapid decomposition and combination thereof will lead to rapid pressurization of shock generation section and generation of shockwaves or pressure waves.

"Detonatable mixture" as used herein, refers to single or multiple reactants that can undergo rapid chemical reactions including detonation, deflagration, rapid decomposition or combination thereof creating a shockwave or pressure wave. One example of a detonatable mixture is the mixture of oxygen, hydrogen and nitrogen gases. Another example of a detonatable mixture is a monopropellant such as nitrobenzene or nitroglycerin. Another example of a detonatable mixture is high concentration hydrogen peroxide that can undergo explosive decomposition after injection into the shock generation section of the apparatus. Selection of a suitable fuel and oxidizer or a single reactant to form the detonatable mixture will be apparent to persons skilled in the art. Non-limiting examples of fuel reactants that can be used to form a detonatable mixture include kerosene, gasoline, methane, natural gas, hydrogen, acetylene, and propylene. Non-limiting examples of oxidizer reactants that can be used to form the detonatable mixture include oxygen, air, a mixture of oxygen and air, a mixture of oxygen and one or more inert gases such as nitrogen, argon or helium, hydrogen peroxide.

"Shock transmitting media", as used herein, refers to a liquid, a multiphase liquid-solid and gas suspension, solid elastomers a paste and other forms of material that can transmit hydrodynamic shock or acoustic waves. One example of a shock transmitting media is water which has a low attenuation coefficient allowing transmission of shock wave or acoustic wave with very small loss of shock wave energy. Another example of shock transmitting media is elastomer such as Aqualene, silicone rubber or solid plastic such polystyrene that have low acoustic attenuation coefficients.

"Impedance" means "acoustic impedance" that can be calculated by multiplying density and sound speed of the media.

"Membrane" is a part of the shock generation section of the apparatus that transmits shock waves or acoustic waves from the shock generation section into the shock transmitting media of the device.

Figures 1, 1A:
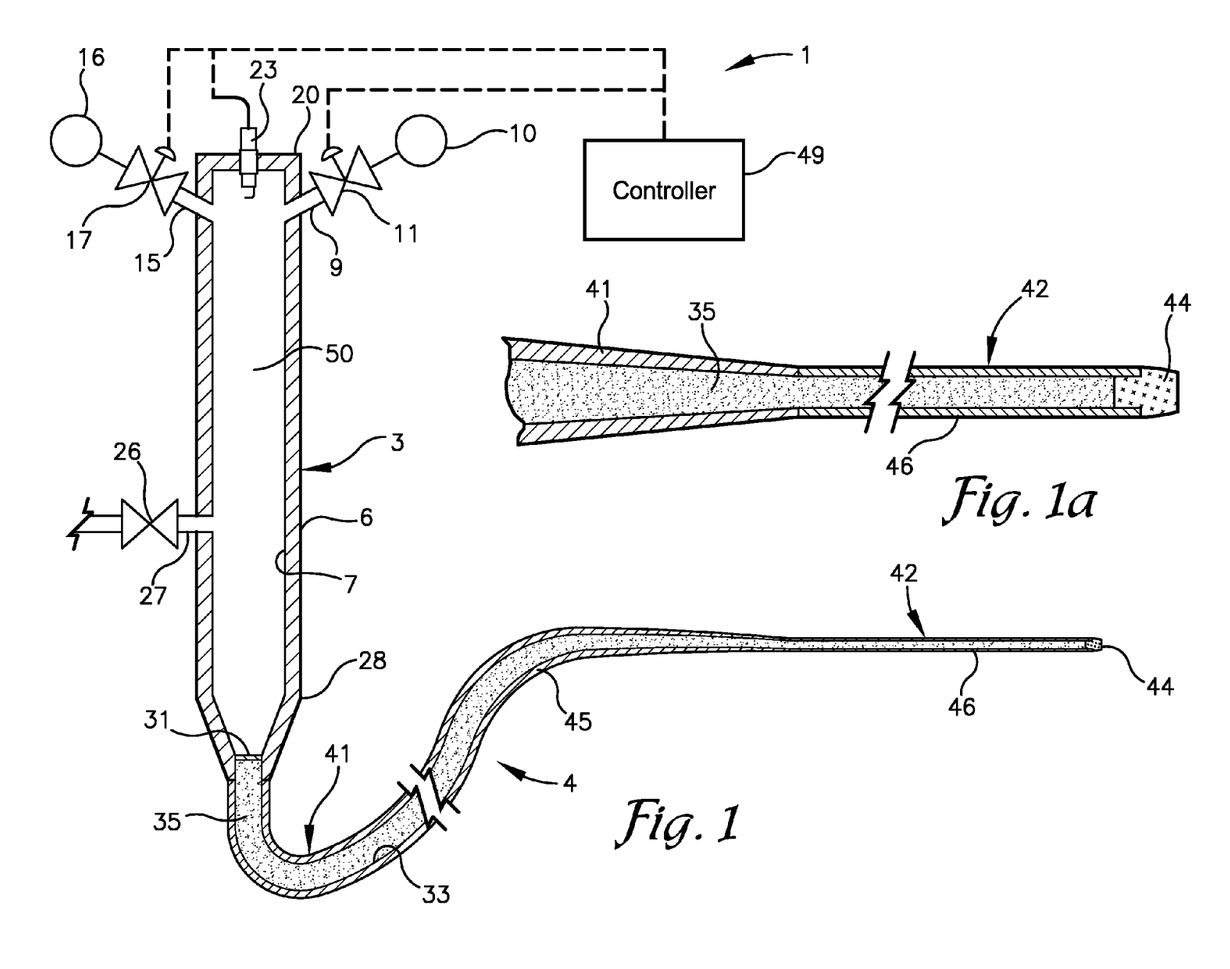
FIG. 1 is a schematic, cross-sectional illustration of a stereotactic shockwave surgical (SSS) apparatus including a cylindrical shockwave generation section with a shockwave guide including a needle for insertion into a patient connected thereto with a shockwave transmitting membrane separating a passageway through the shockwave guide from a shockwave generation chamber in the shockwave generation section.
FIG. 1a is a schematic, cross-sectional illustration of a distal end of the shock wave guide showing a shock transmitting liquid sealed within the internal passageway of the shock wave guide by a shock transmitting elastomeric plug.

Referring now to the invention in more detail, FIG. 1 schematically illustrates a first embodiment of a therapeutic apparatus 1 for treatment of body tissue using shock waves which may be referred to as a Stereotactic Shockwave Surgery (SSS) apparatus. The SSS apparatus 1, is configured for the repetitive generation of shock waves to be transmitted to or against selected tissue or portions of the body for treatment.

The SSS apparatus 1 includes a shock generation section 3 in which shock waves are generated and a wave transmission section or wave guide assembly 4 through which the shock waves are transmitted and directed to the tissue to be treated. The shock generation section 3 generally comprises a pressure vessel having a vessel wall 6 surrounding a detonation chamber 7. An oxidizer is injected into the detonation chamber 7 through a oxidizer feed line 9 extending from an oxidizer storage tank 10. An oxidizer control valve 11 mounted on feed line 9 controls the flow of oxidizer into the detonation chamber 7. Fuel is injected into the detonation chamber through fuel line 15 extending from fuel storage tank 16 through fuel control valve 17. In the embodiment shown, the oxidizer feed line 9 and fuel line 15 extend through the vessel wall 6 near a first or closed end 20 of the shock generation section 3.

A spark plug 23 is mounted in the vessel wall 6 and extends into the detonation chamber 7 near the inlets for the oxidizer feed line 9 and the fuel line 15. A pressure relief valve 26 is mounted on an exhaust line 27 connected to the vessel 3 near a second or distal end 28 thereof which tapers inward. A shock transmitting membrane 31 extends across the distal end 28 of the vessel 3 separating the detonation chamber 7 of vessel 3 from a wave guide passageway 33 formed in and extending through the wave guide assembly 4. The wave guide passageway 33 is filled with a shock transmitting media 35.

The wave guide assembly 4 as shown in FIGS. 1 and 1a includes a flexible conduit 41 and a shock guide needle 42 with an end cap or plug 44 closing off the end of the needle 42 and encapsulating the shock transmission media 35 within the wave guide passageway 33. The shock transmission media 35 preferably comprises a media exhibiting a low acoustic attenuation coefficient such as water.

The cylindrical wall 45 forming conduit 41 and surrounding the wave guide passageway 33 is preferably made from a high impedance material for more effective shock containment. Wall 45 can be made from flexible or rigid material or a combination of flexible and rigid material to facilitate shock delivery to a selected body location. For compatibility with Magnetic Resonance Imaging (MRI) the cylindrical wall 46 forming the shock guide needle 42 is preferably made from nonmagnetic material such as Titanium or other nonmagnetic structural materials. The end cap 44 is formed from a material selected to allow transmission of shock waves therethrough from the wave guide passageway 33 to tissue against which the end cap 44 is positioned with minimal loss of energy and can be made from elastomer or metal.

An example of the SSS apparatus 1 shown schematically in FIG. 1 and FIG. 1a may have a cylindrically shaped shock generation section or vessel 3 from the spark plug 23 to the exhaust line 27 with a converging diameter proximate the second end 28 of the vessel, from the exhaust line 27 to the shock transmitting membrane 31. The diameter of the shock generation section 3 may be 2.5 cm at the first end 20 and 1 cm adjacent the membrane 31 with an internal height or length of 15 cm resulting in a volume of the detonation chamber 7 of approximately 70 cm$^3$.

The flexible conduit 41 of the wave guide assembly 4 has a tubular geometry with a circular cross section of 1 cm in diameter from the area proximate the membrane 31 that converges to a circular cross section of 3 mm adjacent the shock needle 42 which generally maintains a constant cross section of 3 mm. The length of the flexible conduit 41 may be approximately 5 meters and the length of the shock needle 42 may be approximately 10 cm. The total internal volume of the flexible conduit 41 and the shock needle 42 is then approximately 390 cm$^3$.

The walls of shock generation vessel 3 may be made from 1 cm thick high strength steel. To lower losses of shock wave energy, the wall 45 forming conduit 41 may be made of a high acoustic impedance material such as tungsten-carbide-cobalt cermet formed 3 mm thick. Other examples of high acoustic impedance material that can be used in construction of the wave guide assembly 4 including the conduit 41 and shock needle 42 include aluminum oxide, tungsten, and tantalum. The needle wall 46 may be formed from tantalum with a wall thickness of 2 mm. Tantalum is a preferred material because it is nonmagnetic and biocompatible. To make the conduit 41 of the wave guide assembly 4 flexible it can be assembled from interconnecting smaller sections of rigid high acoustic impedance material. Alternatively, the conduit 41 could be made from flexible a plastic material that is loaded with tungsten powder to increase the impedance through the conduit wall 45 and thus reduce shock wave energy loss. As used herein, the conduit wall 45 and the needle wall 46 surrounding the wave guide passageway 33 may be referred to collectively as the passageway enclosure or wave guide passageway enclosure.

The membrane 31 may be made from high strength steel having a thickness of approximately 3 mm. The membrane 31 is welded to the vessel wall 6 of the shock generation section 3 across the second end 28 thereof. The spark plug 23 and oxidizer control valve 11 and fuel control valve 17 are linked to a controller 49 which is programmed to control the operation of these components.

Operation of the SSS apparatus 1 schematically shown in FIGS. 1 and 1a starts with the insertion of shock needle 42 into tissue to be treated with the cap 44 placed in direct contact with the body tissue that will be exposed to the shockwaves. When the shock needle 42 is inserted and in contact with targeted body tissue, fuel and oxidizer are injected into the detonation chamber 7 of the shock generation vessel 3. The fuel and oxidizer are selected so that the mixture is detonatable and their injection through control valves 11 and 17, respectively, is metered by the controller so that the resulting detonatable mixture 50, upon detonation, will form a shock wave of sufficient intensity that when transmitted through the wave guide assembly 4 and end cap 44 will result in a selected therapeutic effect. Such effect may include physical disruption of and killing of cancer cells, increasing cells walls permeability for drug delivery and other effects.

After injection of a desired or selected amount of the detonatable mixture, ignition of and detonation of the detonatable mixture 50 generates a detonation wave within the detonation chamber 7. The detonation wave propagates through the volume of the detonation chamber 7 until it reaches the membrane 31 separating the detonation chamber 7 from the shock transmission media 35 in the wave guide passageway 33. A portion of the shock wave reflects back through the detonation chamber 7 and another portion passes through the membrane or interface 31, into the wave guide assembly 4. The shock transmitted into the wave guide assembly 4 propagates through the shock transmitting media 35 with low acoustic attenuation coefficient such as water. The shock amplitude losses during propagation will be also minimized by forming the walls 45 and 46 of the conduit 41 and needle 42 respectively from materials with high acoustic impedance. The shock amplitude will increase in the conduit through which the diameter of the wave guide passageway 33 converges towards the shock needle 42 and the shock will further propagate through the needle 42 and needle cap 44 into the body tissue.

When the average pressure in the detonation chamber reaches a preset value the pressure release valve 26 will open and detonation products will be vented to atmosphere. Due to inertia of the pressure relief valve 26 it will open after the main shockwave is generated and thus will not interfere with the shock generation process. The pressure relief valve 26 can be selected to have an opening time as fast as 30 milliseconds when the time of generation, propagation and reflection of the shockwave will be approximately 2 milliseconds which will assure that detonation chamber 7 will not lose pressure during the shock generation process. Pressure relief can also be facilitated without use of a pressure relief valve by selecting the size of opening 27 so that during detonation very small amounts of the detonation products will be exhausted thought this opening due to the short duration of the process and most of the detonation products will be exhausted after the shockwave is transmitted into wave guide passage 35. Exhausted gases can be captured, filtered and release into the surrounding atmosphere when not harmful. After the pressure in the detonation chamber 7 drops to a preset value, the pressure relief valve 26 closes, sealing the volume of the detonation chamber 7. At this point, the steps of injection and detonation will be repeated to generate another shock wave. The shock generation steps can be repeated at a frequency selected to obtain the best therapeutic effect for the chosen application. This frequency is controlled by controller 49.

The amount of energy transferred and reflected during a single detonation will be a function of the physical parameters or properties of the detonation wave, the membrane 31, and the shock transmission media 35 in the wave guide passageway 33. Parameters of the detonation mixture 50, membrane 31, and media 35 can be suitably selected by persons skilled in the art in such a way that a substantial portion of shockwave energy generated in the shock generation section 3 is transmitted into the wave guide assembly 4 and further into body tissue via shock needle 42 and needle cap 44.

The membrane 31 of the apparatus as shown in FIG. 1 is preferably constructed to sustain the pressure load produced by repeated detonation in the detonation chamber 7 and have minimal thickness and impedance to allow transmission of the shock waves from the shock generation section 3 to the wave guide assembly 4 of the apparatus 1. Thickness of the membrane 31 will be a function of pressure in the shock generation section 3 and material strength of the membrane material, and may range from 0.5 mm to 50 cm.

Figures 2, 2A, 3, 3A:
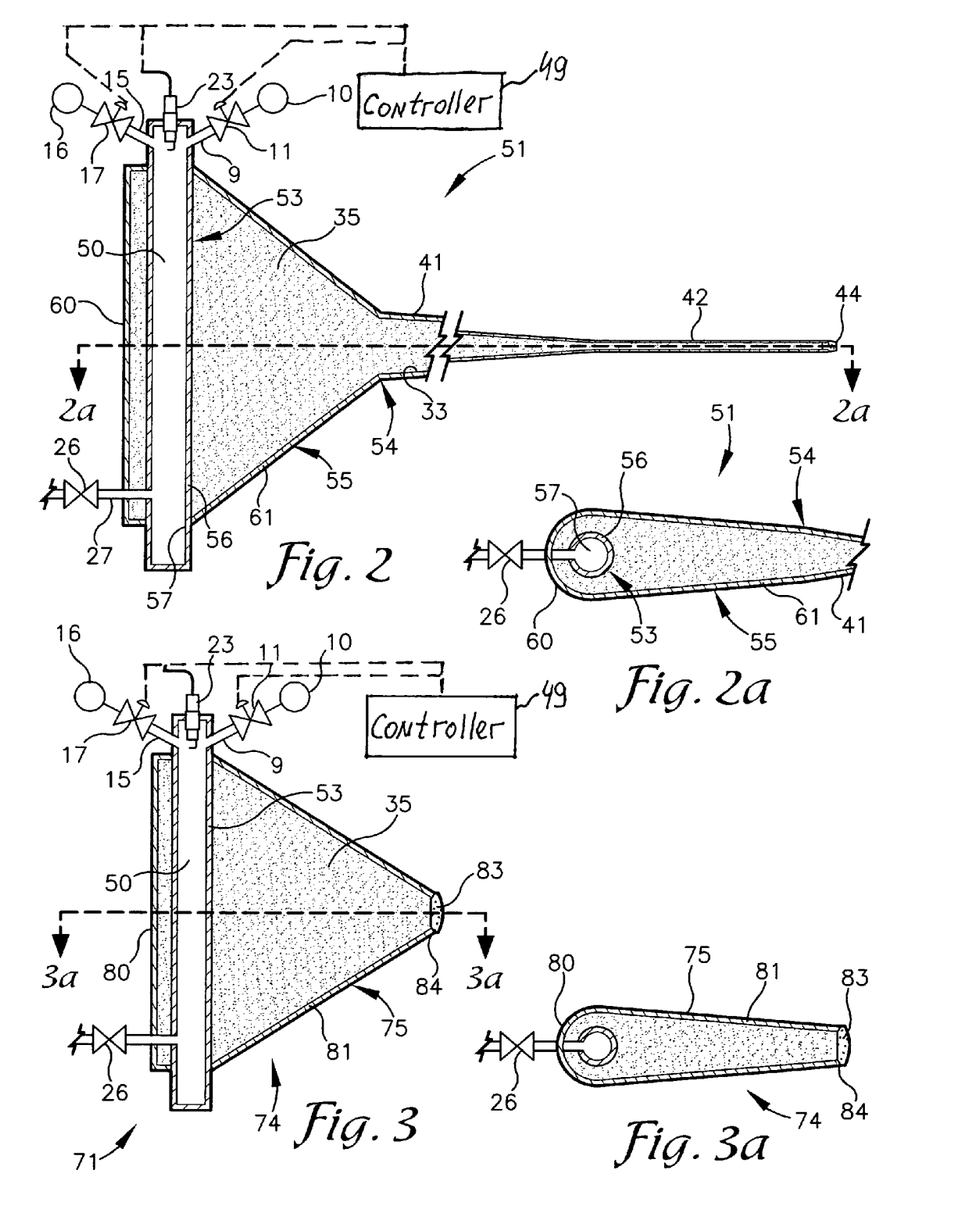
FIG. 2 is a schematic, cross-sectional illustration of a second embodiment of the stereotactic shockwave surgical apparatus in which shock transmitting media surrounds the shock generation section allowing direct transmission of shockwaves from the shock generation section into the shock transmitting media through the walls of the shock generation section and then into a shockwave guide.
FIG. 2a is a schematic, cross-sectional view of the surgical apparatus taken along line 2a-2a of FIG. 2.
FIG. 3 is a cross-sectional schematic view of a third embodiment of the stereotactic shockwave surgical apparatus in which shock transmitting media maintained in a wave focusing section surrounds the shock generation section allowing direct transmission of shockwaves from the shock generation section into the shock transmitting media through the walls of the shock generation section wherein the wave focusing section converges to a tip which may be positioned in direct contact with an area of a patient to be treated with shockwaves.
FIG. 3a is a schematic, cross-sectional view of the surgical apparatus taken along line 3a-3a of FIG. 3.

An alternative embodiment of a SSS apparatus 51 is shown in FIGS. 2 and 2a having a shock generation section or vessel 53 that is inserted within or surrounded by an enlarged portion of a wave guide assembly 54 which may be described as or referred to as a shock reception section or wave focusing section 55. A substantial portion of the shock generation vessel 53 extends within the wave focusing section 55. In describing the embodiment of the shock transmitting apparatus 51 shown in FIGS. 2 and 2a and the additional embodiments shown in subsequent figures, common elements may be identified by the same reference numbers used in describing the embodiment shown in FIGS. 1 and 1a.

Referring again to FIGS. 2 and 2a, the wave guide assembly includes a wave focusing section 55 in addition to a flexible conduit 41 and shock needle 42 with cap or tip 44. Shock transmitting media 35 surrounds the cylindrical wall 56 of the shock generation vessel 53. Shockwaves generated in the detonation chamber 57 of vessel 53 are transmitted into the shock transmitting media 35 through the cylindrical wall 56 of vessel 53. The shockwaves deflect off of the end wall 60 and converging sidewall 61 of the wave focusing section 55 so as to be directed into the flexible conduit or intermediate section 41 of the wave guide assembly 54. The shock waves continue through the flexible conduit 41 to then through the shock needle 42, and out the needle cap 44 exiting into body tissue to be treated.

In the embodiment shown schematically in FIGS. 2 and 2a, the cylindrical wall 56 of the shock generation vessel 53 is preferably made from low impedance material such as aluminum and designed to contain multiple detonations and to allow efficient shock transmission through the cylindrical wall 56. Another example of a material with high tensile strength and low impendence that can be used for construction of the shock generation vessel 53 that allow efficient transmission of shockwaves is graphite composite material. In this case the inner walls of detonation chamber 53 can be coated with metal to protect carbon and elastomeric materials of graphite composite from exposure to high temperature detonation products and from oxidation. In the embodiment shown in FIG. 2 the end wall 60, converging wall 61, conduit wall 45 and shock needle wall 46 are preferably made from high impedance material such as Aluminum Oxide, Tungsten, or Tantalum. To further reduce propagation of shockwaves through the shock guide wall 45 and needle wall 46, either or both may incorporate one or more layers of material with a high acoustic attenuation coefficient such as: composite materials, porous materials or materials with vacuum filled layers. As a function of detonation gas containment, shock propagation requirements and material properties, the wall thickness of the shock generation vessel 53 may range from 0.5 mm to 50 cm. As a function of shock propagation requirements, device design and material properties, the wall thickness of walls 60, 61, 45 and 46 may range from 0.5 mm to 50 cm. As an example of one possible configuration of the shock transmission apparatus 51, shown schematically in FIG. 2, the shock generation vessel 53 will have a 2 cm diameter and will be 20 cm long. The back side or end wall 60 will be cylindrical, 4 cm in diameter and 16 cm long. The converging wall 61 will converge from 16 cm to 3 cm diameter and the guide conduit 41 will be 1 m long and converge from 3 cm to 3 mm in diameter, which is the diameter of the shock needle 42.

A third embodiment of a shock transmitting apparatus 71 is shown schematically in FIG. 3. The SSS apparatus 71 is similar in construction to the apparatus 51 shown in FIGS. 2 and 2a with the guide conduit 41 and needle 42 removed, leaving the shock generation vessel 53 and a wave guide assembly 74 generally comprising only a wave focusing section or structure 75 with a back side wall 80 and a front converging wall 81. The shock generation vessel 53 extends through and is surrounded by the wave focusing structure 75. Shock transmitting media 35, which can be in either liquid or solid form surrounds the portion of the shock generation vessel 53 extending through the wave focusing structure 75.

An end cap or shock transmitting cap 83 is secured across the narrow, distal end 84 of the converging wall 81 of the wave focusing structure 75, across an opening therethrough. The end cap 83 is formed from a material selected to allow transmission of shock waves therethrough from the wave focusing structure 75 to tissue against which the end cap 83 is positioned with minimal loss of energy and can be made from elastomer or metal. The embodiment 71 with the shock transmitting cap 83 connected to the end of the converging wall 81 is particularly well adapted for extracorporeal application of shock waves and for improved drug delivery where applications of shock waves will improve cells permeability. In an example of a shock transmitting apparatus 71 as shown in FIGS. 3 and 3a the shock generation vessel 53 may have a diameter of 1 cm and a length or height of 10 cm. The back side or end wall 80 of the wave focusing section 75 is hemicylindrical with a diameter of 2 cm and a length or height of 8 cm. The converging wall 81 of the wave focusing section 75 may converge from 8 cm in width or diameter at the transition with the end wall 80 to 1 cm in diameter at the shock application cap 83.

Figure 4:
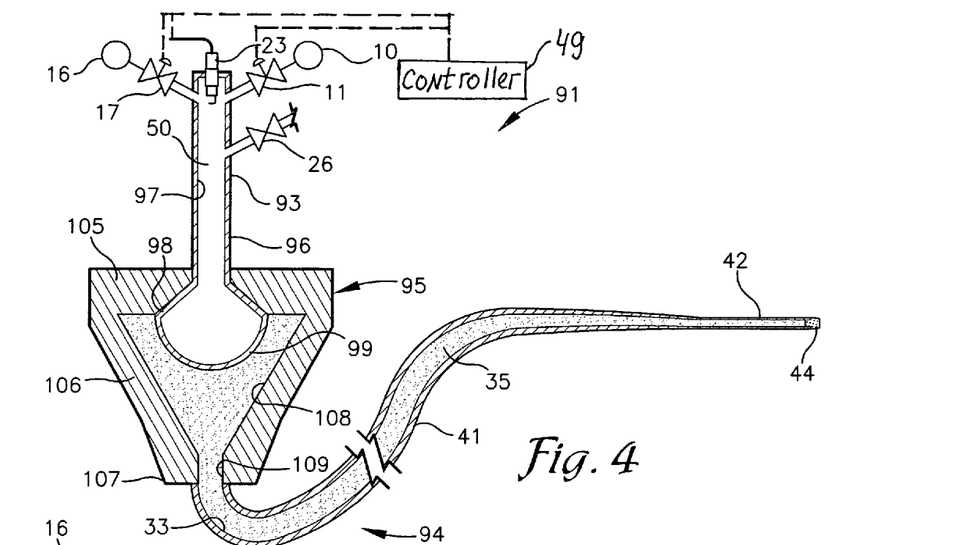
FIG. 4 is a cross-sectional schematic view of a fourth embodiment of the stereotactic shockwave surgical apparatus in which the shock generation and shock transmission sections have diverging and converging cross sections respectively in order to maximize shock transmission, to manage the shock wave positive phase duration and to amplify or reduce shock wave peak pressure.

FIG. 4 discloses a further alternative embodiment of a SSS apparatus including a shock generation vessel 93 and a wave guide assembly 94 having a wave focusing section 95 in addition to the flexible guide conduit 41 and needle 42. A vessel wall 96 surrounds the detonation chamber 97. A lower end 98 of the vessel wall 96 of the shock generation vessel 93 flares or diverges outward. A shock transmission membrane 99 extending across the flared end 98 of the vessel 93 is hemispherical and curves outward relative to the detonation chamber 97. In this embodiment the relief valve 26 is located toward an upper end of the shock generation vessel 93.

The wave focusing section 95 includes and end wall 105, a converging sidewall 106 and an outlet end 107. The end wall 105 and converging sidewall 106 surround a wave focusing chamber 108. The wave focusing chamber 108 is generally defined by the converging sidewall 106 and converges from the end wall 105 toward the outlet end 107 of the wave focusing section 95. The converging sidewall 106 and wave focusing chamber 108 are generally frusto-conical in shape, converging toward the flexible guide conduit 41 which is connected to the outlet end 107 of the wave focusing section 95. A guide channel 109 of generally uniform cross-section extends from the narrow end of the wave focusing chamber 108 to an outlet through the outlet end 107 of the wave focusing section 95.

A distal end of the shock generating vessel 93 extends through the end wall 105 of the wave focusing section 95 with the shock transmitting membrane 99 positioned at the interface between the end wall 105 and the wave focusing chamber 108. The wave focusing chamber 108 is filled with the shock transmission media 35. The wave focusing section 95 is constructed from a high impedance material such as tungstencarbide/cobalt cermet or similar materials. In one example of the SSS apparatus as shown schematically in FIGS. 4, 5 and 6, the shock generation vessel 93 is 1 cm in diameter and 20 cm long. The hemispherical membrane is 3 cm in diameter. The shock reception chamber has a trapezoidal conical geometry with a width or diameter of 5 cm in the area of the membrane and a diameter of 1 cm adjacent the wave guide channel 109. The diameter through the wave guide channel 109 is 1 cm. The guide conduit 41 preferably is 1 m to 2 m long with a diameter that converges from 1 cm to 3 mm. The shock needle 42 is preferably 3 mm in diameter.

The membrane 99 and walls 96 of the shock generation vessel 93 can be cooled to prevent damage from excessive heating. For example, an operator can time the detonations in the vessel 93 so excessive heat is removed to the surroundings through natural convection. The shock transmitting media 35 may also be circulated so that heat is absorbed by the media 35 without a significant increase of its temperature. The media 35, may be circulated and cooled outside of the wave guide assembly, such as assemblies 4, 54, 74 or 94, to prevent the media 35 from overheating.

Figure 5:
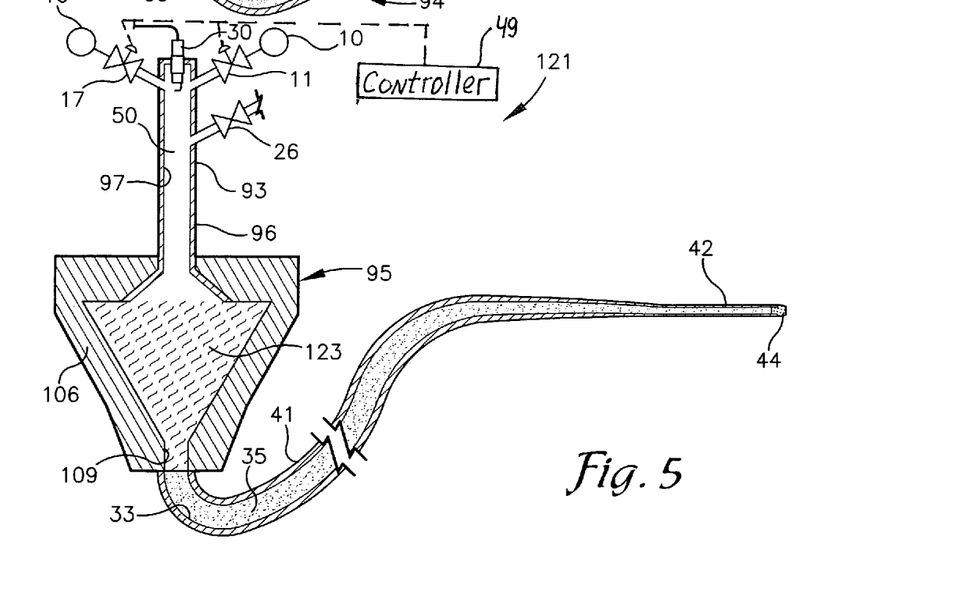
FIG. 5 is a cross-sectional schematic view of a fifth embodiment of the stereotactic shockwave surgical apparatus in which the shock generation section is in direct contact with a solid media contained in a shock transmission section which in turn is in contact with a liquid shock transmission media contained in the shock guide.
Figure 6:
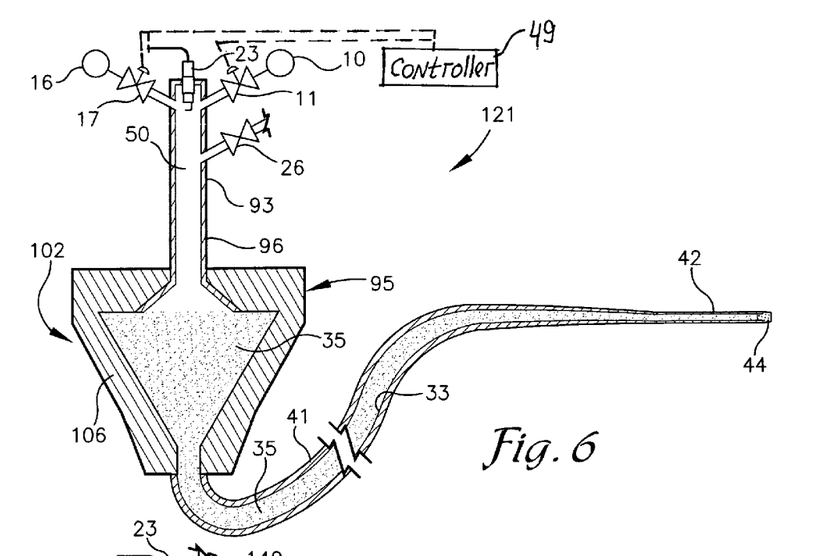
FIG. 6 is a cross-sectional schematic view of a sixth embodiment of the stereotactic shockwave surgical apparatus which transmits shock waves directly into a shock wave transfer media contained in the shock transmission section and in the shock guide.

FIG. 5 is a schematic illustration of a modified version 121 of the SSS apparatus 91 shown in FIG. 4, in which the detonation chamber opens directly into the wave focusing chamber 108 without a shock transmission membrane 99 extending therebetween. Wave focusing chamber 108 is filled with an elastomer 123 that has low acoustic impendence and low acoustic attenuation parameters. Examples of elastomer that can be used to fill chamber 108 include polyethylene, polyurethane, Nylon or ethyl vinyl acetate that have impedances comparable to the impedance of water. Standard methods can be suitably selected by persons skilled in the art with the aid of no more than routine experimentation to protect elastomer from heat exposure from detonation products. The guide conduit 41 is then filled with the liquid shock transmission media 35. Alternatively, both the wave focusing chamber 108 and the rest of the wave guide passageway 33 can be filled with the liquid shock transmitting media as shown schematically in FIG. 6.

Figure 7:
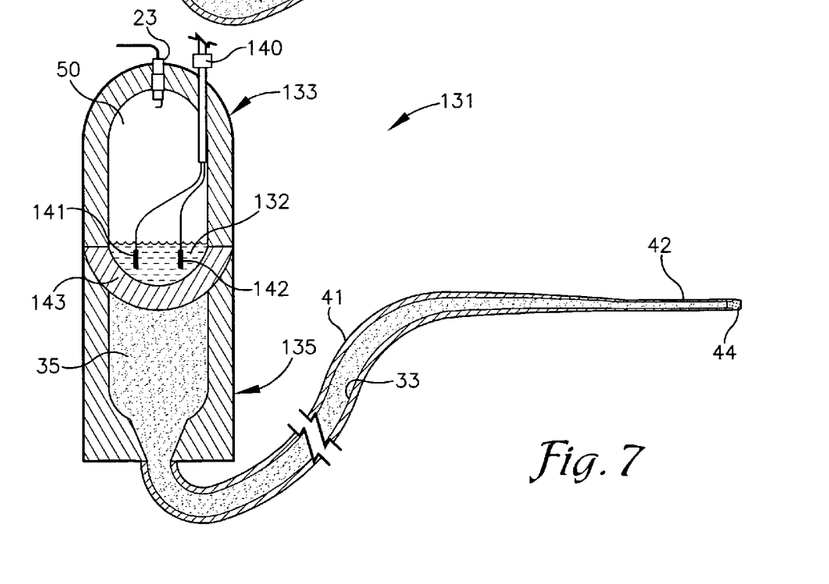
FIG. 7 is a cross-sectional schematic view of a seventh embodiment of the stereotactic shockwave surgical apparatus in which a detonatable mixture used in the shock generation section is produced by electrolysis of water contained in this section.

FIG. 7 schematically illustrates another embodiment of a SSS apparatus 131 in which the detonatable mixture 50 is a hydrogen-oxygen gas mixture that is generated by electrolysis of water-based electrolyte 132. Examples of water based electrolytes include: water/sulfuric acid (H2SO4), water/potassium hydroxide (KOH), and water/sodium hydroxide (NaOH) electrolytes. In the embodiment shown in FIG. 7, the shock generation vessel 133 is partially filled with electrolyte 132 to a level sufficient to submerge an anode 141 and a cathode 142 extending into the vessel 133 through a sealed conduit 140. An electric voltage is conducted through the anode 141 and cathode 142 to decompose the water to hydrogen gas and oxygen gas upon the supply of sufficient electrical energy. After a sufficient amount of a detonatable mixture 50 of the hydrogen and oxygen gas is generated, the mixture 50 is ignited by spark plug 23 generating a detonation and shockwave that is transmitted through shock transmitting membrane 143 into a wave focusing section 135 and then through the guide conduit 41 and shock needle 42 which is inserted into tissue such as a body organ to apply shock waves thereto specific body. Insertion and placement of the needle may be guided by MRI or other imaging systems.

For example needle 42 may be inserted into the brain where the needle cap 44 is placed in the vicinity of or in direct contact with a cancerous tumor. After detonation, the detonation products mainly comprising water vapor can be condensed back into water through cooling of the shock generation vessel 133 and the process can be repeated. A critical advantage of this embodiment is that it will not require a supply of detonatable mixture 50 from an outside source and the detonation products are not vented into the atmosphere. Thus, this type of device will be particularly attractive for use in small operating rooms or in a doctor's office environment. The apparatus 131 shown schematically in FIG. 7 can be implemented for operation at a wide range of shock wave pressure, shock repeating frequency and device scales. The shockwave pressure generated in the device schematically shown in FIG. 7 will be a function of the density and pressure of the detonatable mixture that will be produced as a result of electrolysis. It is foreseen that the density of the detonatable mixture produced by electrolysis prior to initiation may range from 0.1 to 1000 kg/m$^3$.

Figure 8:
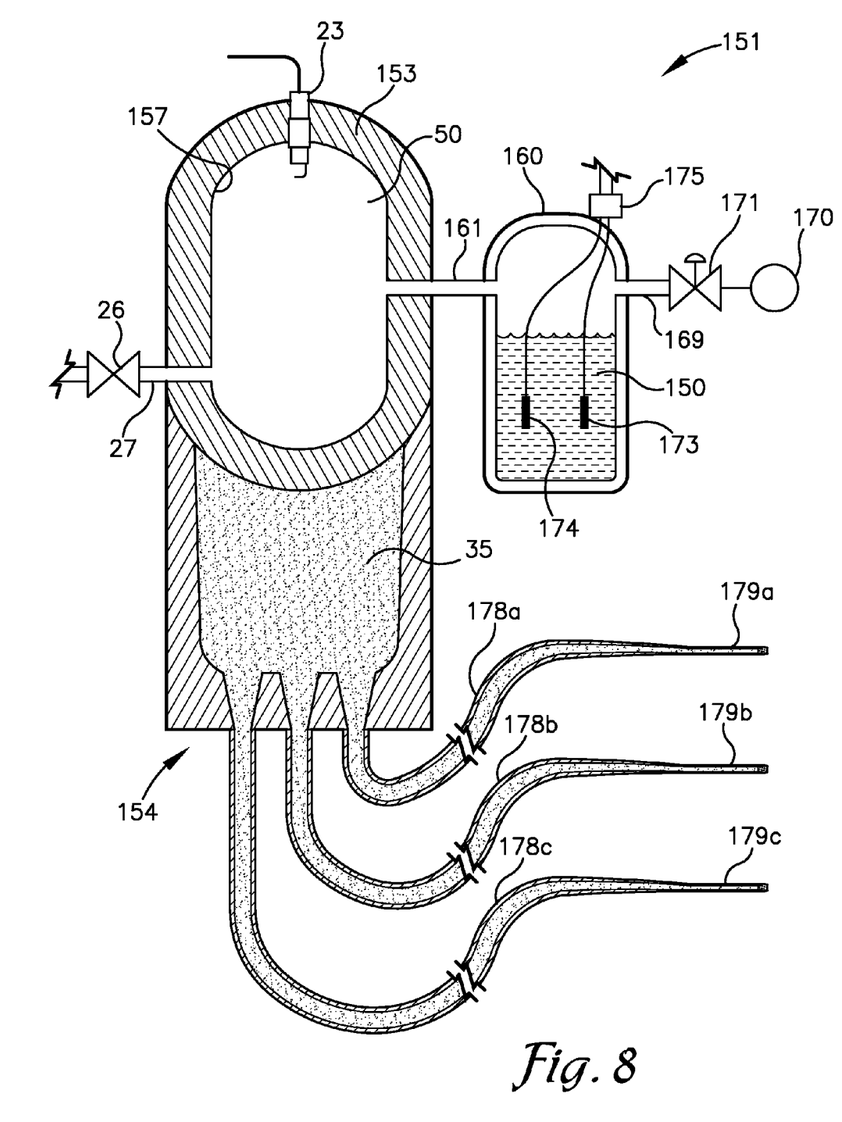
FIG. 8 is a cross-sectional schematic view of an eighth embodiment of the stereotactic shockwave surgical apparatus in which a detonatable mixture used in the shock generation section is produced by electrolysis of water in a separate water electrolysis section.

FIG. 8 schematically illustrates another embodiment of a shock transmitting apparatus 151 that is also based on the generation of a detonatable mixture 50 through water electrolysis as shown in the embodiment 131 shown in FIG. 7. However, in apparatus 151, the electrolysis of water is done in a separate electrolysis vessel 160 that is connected to the internal volume of the shock generation vessel 153 through a supply conduit 161. Water-based electrolyte 150 is supplied to the electrolysis vessel 160 through a supply line 169 extending from a water-based electrolyte tank 170 and through a flow control valve 171. Enough electrolyte 150 is supplied to the electrolysis vessel 160 to submerge an anode 173 and a cathode 174 extending therein through conduit 175. Detonation products may be vented through an exhaust line 27 in shock generation vessel 153 the when the pressure therein exceeds the set pressure of relief valve 26. An advantage of this embodiment is that it will require supply of only water-based electrolyte 150 and electricity for generation of shock waves and will not require cooling for water regeneration as in the embodiment shown in FIG. 7.

FIG. 8 also demonstrates that the wave guide assembly 154 for a SSS apparatus such as apparatus 151, may comprise a plurality of wave guide conduits, such as conduits 178$a$-$c$ and a plurality of needles such as needles 179$a$-$c$. Wave guide conduits 178$a$-$c$ may be of similar construction as conduit 41 and needles 179$a$-$c$ may be of similar construction as needle 42. The multiple shock needles 179$a$-$c$ can be inserted near same body tissue or object such as cancerous tumor to produce shock focusing effect by simultaneous exposure of the tumor to shock waves from multiple sources. The shock needles 179$a$-$c$ can be also inserted into different body locations. It is foreseen that the detonable 50 mixture can be supplied by multiple electrolysis vessels 160 or a single electrolysis vessel 160 can supply detonatable mixture 50 into multiple shock generation vessels 153.

Figure 9:
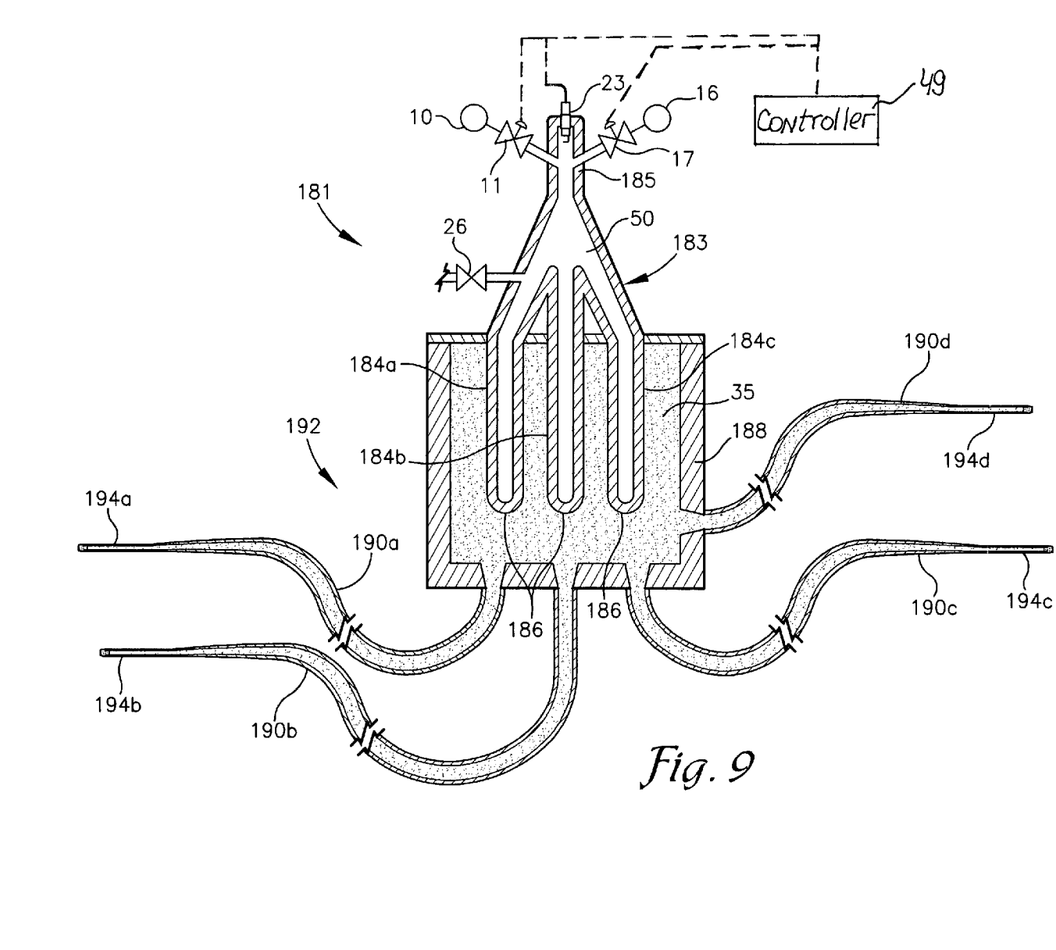
FIG. 9 is a cross-sectional schematic view of a ninth embodiment of the stereotactic shockwave surgical apparatus in which the shock generation section is split into multiple, connected, closed-ended subsections that are immersed into the shock transmitting media which transmit shockwaves through multiple shock guides to multiple application sites.

FIG. 9 schematically illustrates another embodiment of a SSS apparatus 181. The apparatus 181 includes a shock generation vessel 183 that is formed by multiple cylindrical extensions or branches 184$a$-$c$ branching out from and connected to a single reactant initiation tube or trunk 185. The cylindrical branches 184$a$-$c$ terminate in semispherical end caps 186. The branches extend into and are surrounded by a wave distribution or shock reception enclosure 188 from which a plurality (four shown) of wave guide conduits 190$a$-$d$ extend. The wave distribution enclosure forms part of the wave guide assembly 192 along with the conduits 190$a$-$d$ and needles 194$a$-$d$ connected thereto. Oxidizer and fuel are injected through control valves 11 and 17, respectively, and fill the internal volume of the shock generation vessel 183 with a detonatable mixture 50. Ignition of the detonatable mixture 50 by spark plug 23 initiates a detonation wave that will propagate into all of the cylindrical branches 184, each generating shockwaves that will transmit into the media 35 within wave distribution enclosure 188. Constructive and destructive interference of these high intensity waves will produce shock waves and acoustic waves that will be transmitted through the wave guide conduits 190$a$-$d$ to an intended area of application to the body. The apparatus 181 shown schematically in FIG. 9 can be implemented for extracorporeal or intra-corporeal therapeutic medical application of shock waves.

The various embodiments of the SSS apparatus, produce high intensity shock waves in the shock generation section 3 that transmit through the media shock transmitting media 35 in the shock guide passageway 33 of the wave guide assembly 4 including through the guide conduit 41 and the shock needle 42 and through the needle cap 44 and are of sufficient amplitude and shock pressure positive phase duration to produce a therapeutic medical effect in the body tissue that is in vicinity of the needle cap 44. The SSS apparatus as disclosed herein provide scalable, safe, localized and cost effective apparatus and therapeutic methodology that consists of using a detonatable or other reactive mixture 50 that can be repeatedly injected into a shock generation chamber 7 that is designed to contain detonation products and transmit shockwaves through the shock transmission membrane 31 into the wave guide passageway 33 filled with the shock transmission media 35 and through the shock needle 42 that is inserted into a patient's body where the needle cap 44 will be in direct contact with tissue to be treated, such as a cancerous tumor. The shock generation vessel 3 of the apparatus 1 can be filled with a stoichiometric mixture of oxygen and natural gas at 2 MPa (mega Pascal) initial pressure and approximately 0.03 g/cc initial density. This mixture is detonatable thus initiation with spark plug 23 will cause detonation. The resulting detonation wave will create a shockwave in the shock generation section 3. Typically, a detonation wave propagating through a 2 MPa detonatable mixture will have approximately 60 MPa peak pressure, approximately 2 km/sec shock velocity, and approximately 0.2 g/cc density. The amount of shock wave energy transmitted to the transmission media 35 is a function of the media impedance. In one example of operational parameters of apparatus 1 the transmission media 35 is water where at a detonation of 2 MPa of a mixture of natural gas and oxygen will generate a hydrodynamic shock wave with peak pressure of approximately 120 MPa. This shock wave when transmitted through needle cap 44 will result in the cancer cells being permeable to anti-cancer drugs or killing cancer cell.

Examples of use of the various embodiments of the SSS apparatus disclosed herein include:
  Local breakdown of fatty cells and tissues without heat damage for treating lipomas of the nervous system.
  Treatment of parasites or localized infection processes (brain abscesses) using local shockwaves to avoid the risk of dissemination that is prevalent with surgical interventions traditionally used for such afflictions.

Treatment of arachnoid and colloid cysts by shockwave disruption of biofilms.

Controlled application of shockwaves to break down adhesions in brain ventricles and fibrotic tissues formed around implanted ventricular catheters.

Dissolving intra-ventricular and intra-parenchymal blood clots.

New modes of local or systemic drug delivery directly to cells through shockwave-enhanced cell permeability.

Thus there are critical advantages in the use of SSS based surgical instruments that apply high-intensity shockwaves to small areas without extensive thermal or mechanical disruption.

One of the critical advantages of SSS technology is to allow direct and localized exposure of tumor or other body tissue cells to high-pressure, short-duration shockwaves. In contrast with other local shock generation methods that use laser irradiation or small electrical discharges, SSS will not have harmful and disruptive thermal side effect because shockwaves will be delivered to the area to be treated using small diameter shock needles. For example, and without limitation, the external diameter of the shock needle 42 may be 2 mm to 10 mm with an internal diameter of 1 mm to 8 mm. Shockwave transmission through the 1 mm to 10 mm diameter cap 44 will assure that only the area in direct contact with and in the immediate vicinity with the cap 44 will get maximum exposure to shock pressure, since the shock will rapidly decay with distance from what is essentially a point source.

Another critical advantage of the present invention is its scalability to a wide range of sizes based on medical treatment needs. The size of the shock generation vessel, wave focusing section, shock guide conduit, shock needle and needle cap in the embodiments shown schematically in FIGS. 1 through 9 can be selected to accommodate needs in terms of shock amplitude and duration required to produce therapeutic effect. For example, and without limitation, the detonation chamber of the shock generation vessel, such as vessels 3, 53 or 93, can have a volume of 1 $cm^3$ to 1000 $cm^3$ for generation of localized shock waves for medical treatment for shock therapy or drag delivery or 0.1 liters to 100 liter for an SSS shock generation system that delivers shockwaves to multiple shock guides in hospital setting. Without limitation, the length of the shock guide conduit, such as conduits 41 or 190 can be 10 cm to 10 m long where the volume of shock transmitting media is 0.5 $cm^3$ to 10 liters. Based on processing needs, the shock generation vessel and the wave guide assembly may have one of the following: equal volumes; the shock generation vessel may have a volume that is larger than the waver guide assembly; or the shock generation vessel may have a volume that is smaller than that of wave guide assembly.

The critical advantage of the present invention without limitation is its ability to generate shockwaves and acoustic waves with a wide range of parameters that will be beneficial for killing cancer cells, killing micro-organisms, drug delivery, destroying blood vessel plugs, improving bone healing processes and other medical applications. The shock generation vessel can be filled with detonatable reactants to provide a detonatable mixture with an initial density that may range from 0.1 to 1800 kg/m3. Reaction of this mixture in a detonative process or other rapid reaction process in the shock generation vessel will generate shockwaves and/or acoustic waves in the wave guide assembly with peak pressure in the range of 1 to 5000 mega pascals (MPa) and, preferably, between 10 and 2000 MPa.

The design of the shock generation vessel can be implemented in various geometries that allow shockwave reflections and focusing or transmitting with different shock wave or acoustic wave profiles of pressure as a function of time. The design of the wave guide assembly including the wave focusing section, guide conduit and shock needle and the design of the needle cap can be implemented to allow focusing and multiple reflections of the transmitted shock waves that can enhance the efficiency of medical treatment with shock waves.

To facilitate pressure containment and reflections of the shock wave the design of the parts of the shock generation vessel that are not in contact with the shock transmitting media can be made for example from materials with high strength and high impedance, such as metals, cermets, ceramics, polymers, fiber based composites, and combination thereof.

To facilitate pressure containment and transmission of the shockwaves from the shock generation vessel to the wave guide assembly, the membrane, the shock transmitting media and portions of the shock generation vessel in contact with the media can be made for example from materials with high strength and low impedance, such as polymers, suitable fiber-based composites, and thin high-strength materials such as steel and combinations thereof allowing wave transmission from the shock generation vessel to the wave guide assembly and the shock needle.

To facilitate multiple reflections of transmitted shock waves and acoustic waves that will reduce shock energy losses the walls of components of the wave guide assembly including the wave focusing section, the guide conduit and the shock needle can be made for example from materials with high impedance such as tungsten, tungsten carbide, steel, cermets, ceramics, and combinations thereof. To increase wave reflection effectiveness the wall thickness of the components of the wave guide assembly can be suitably selected by persons skilled in the art.

To enhance the killing of microorganisms or cancer cells, prior to treatment with the SSS apparatus, the tissue to be treated can injected with small gas bubbles, drugs, nanoparticles and other reagents. The gas bubbles will reduce effective impedance of the treated tissue and produce additional sheer force on bacteria during and after shockwave propagation, and will produce additional shockwaves due to bubble collapse. All these effects will lead to enhanced killing of cells or microorganisms.

It is also understood that the design of the SSS apparatus without limitation can include multiple shock generation sections operating simultaneously or with a pre-determined time delay and multiple shock guides.

It is also understood that multiple SSS apparatus can operate simultaneously, with or without synchronized time delay for treatment of an area of the body using multiple shock guides.

It also understood that for controlling gas and liquid injection and gas relief processes persons skilled in the art can select valves of different construction such as solenoid valves, rotary valves, piezoelectric valves and others. A person skilled in the art can also design operation of the SSS apparatus where some or all valves will be replaced by properly designed opening that will control for example pressure relief of exhaust. The detonation ignition process can be facilitated by various ignition methods such as a spark plug, laser, glow plug and plasma jet ignition.

While particular embodiments of the present invention have been described and illustrated, it should be understood that the invention is not limited thereto since modifications may be made by persons skilled in the art. The present appli-

Having thus described the invention what is claimed as new and desired to be secured by Letters Patent is as follows:

1. A therapeutic apparatus for treating body tissue, comprising:
   a vessel enclosing a detonation chamber allowing introduction a detonatable and reactive mixture into said detonation chamber through flow control valves controlled by a control system and able to contain detonation products after detonation;
   a spark plug, laser, glow plug or plasma jet ignition system capable to ignite said detonatable mixture in said detonation chamber to form at least one shockwave and/or acoustic wave;
   a wave guide assembly connected to said vessel and having a wave guide passageway formed within a passageway enclosure and converging toward a distal end of said wave guide assembly;
   said wave guide passageway being closed at a distal end of said wave guide assembly by an end cap connected to said passageway enclosure; said end cap adapted to engage body tissue to be treated;
   said passageway allowing transmission of the at least one shockwave and/or acoustic wave generated in said detonation chamber to said end cap; and said end cap formed from material selected to permit the at least one shockwave and/or acoustic wave to be transmitted therethrough to act on body tissue in contact with said end cap.

2. The therapeutic apparatus as in claim 1 further including a membrane separating said detonation chamber of said vessel from said wave guide passageway in said wave guide assembly; said membrane configured for transmitting said shock wave generated in said detonation chamber into said wave guide passageway.

3. The therapeutic apparatus as in claim 1 further including a pressure relief valve or pressure relief outlet connected to said vessel and venting reaction products and detonation products out of said detonation chamber.

4. The therapeutic apparatus as in claim 1 wherein said passageway enclosure includes a flexible wave guide conduit and a needle, said wave guide conduit extending between said vessel and said needle; said needle sized for insertion into body tissue.

5. The therapeutic apparatus as in claim 1 wherein said wave guide passageway is at least partially filled with a wave transmitting media.

6. The therapeutic apparatus as in claim 1 wherein said passageway enclosure includes a wave focusing section, a flexible wave guide conduit and a needle, said wave focusing section extending from said vessel to said wave guide conduit and said wave guide conduit extending between said wave focusing section and said needle; said needle sized for insertion into body tissue.

7. The therapeutic apparatus as in claim 1 wherein the detonatable mixture introduced into the shock generation section undergoes at least one reaction selected from the group consisting of detonation, deflagration, transition from deflagration to detonation, rapid decomposition, and combinations thereof that results in rapid pressurization of the shock generation section.

8. The therapeutic apparatus as in claim 1 wherein pharmaceutical compositions are introduced into the tissue to be subjected to the shock wave in order to increase the therapeutic effects of the shock wave.

9. The therapeutic apparatus as in claim 6 wherein said wave guide passageway in said wave focusing section is at least partially filed with a first wave transmitting media and said wave guide passageway in said wave guide conduit and said needle is filled with a second wave transmitting media.

10. The therapeutic apparatus as in claim 1 wherein said passageway enclosure includes a wave focusing section connected to said vessel and a plurality of wave guide conduits connected to said wave focusing section in communication therewith and a needle connected to a distal end of each wave guide conduit; each of said needles sized for insertion into body tissue.

11. The therapeutic apparatus of claim 1, wherein said vessel is at least partially immersed in the wave transmitting media contained within the wave guide passageway.

12. The therapeutic apparatus as in claim 11 wherein said vessel includes a plurality of shock generation chambers.

13. The therapeutic apparatus as in claim 1, wherein said detonation chamber and said wave transmitting media in said wave guide assembly are not separated by a membrane allowing the at least one shockwave and/or acoustic wave generated in the vessel to directly impact said shock transmission media in said wave guide passageway.

14. The therapeutic apparatus as in claim 1 further comprising a pressure relief valve for venting detonation products from the shock generation vessel and a system controller, said system controller capable to control the sequence of valves opening and closing and detonable mixture ignition processes.

15. A therapeutic apparatus for treating body tissue, comprising:
    a vessel enclosing a detonation chamber allowing introduction a detonatable and reactive mixture into said detonation chamber through flow control valves controlled by a control system and containing detonation products after detonation
    a spark plug, laser, glow plug or plasma jet ignition system capable to ignite said detonatable mixture in said detonation chamber to form at least one shockwave and/or acoustic wave;
    a wave guide assembly including a guide conduit connected to said vessel and a needle connected to a distal end of said guide conduit; said needle sized for insertion into body tissue; said wave guide assembly allowing transmission of the at least one shockwave and/or acoustic wave generated in said detonation chamber to a tip of said needle and into the body tissue in which said needle is inserted.

16. The therapeutic apparatus as in claim 15 further including a membrane separating said detonation chamber of said vessel from said wave guide passageway in said wave guide assembly; said membrane configured for transmitting said shock wave generated in said detonation chamber into said wave guide assembly.

17. The therapeutic apparatus as in claim 15 wherein said guide conduit is flexible.

18. The therapeutic apparatus as in claim 15 wherein said wave guide assembly comprises a plurality of guide conduits each having a needle connected thereto and sized for insertion into body tissue, and said wave guide assembly further comprises a wave focusing section connected between said vessel and said plurality of guide conduits.

19. The therapeutic apparatus of claim 15, wherein said wave focusing section at least partially surrounds said vessel.

20. The therapeutic apparatus as in claim 15 wherein said vessel includes a plurality of shockwaves generation chambers surrounded by said wave focusing section.

* * * * *